US008918166B2

(12) United States Patent
Emese

(10) Patent No.: US 8,918,166 B2
(45) Date of Patent: Dec. 23, 2014

(54) METHOD FOR CALIBRATING A DIAGNOSTIC MEASURING DEVICE

(75) Inventor: Bernhard Emese, Düsseldorf (DE)

(73) Assignee: KGMED GmbH, Zaziwil (CH)

( * ) Notice: Subject to any disclaimer, the term of this patent is extended or adjusted under 35 U.S.C. 154(b) by 105 days.

(21) Appl. No.: 13/391,659

(22) PCT Filed: Aug. 20, 2010

(86) PCT No.: PCT/CH2010/000203
§ 371 (c)(1),
(2), (4) Date: Jun. 7, 2012

(87) PCT Pub. No.: WO2011/022851
PCT Pub. Date: Mar. 3, 2011

(65) Prior Publication Data
US 2012/0271184 A1    Oct. 25, 2012

(30) Foreign Application Priority Data

Aug. 28, 2009   (CH) ...................................... 1336/09

(51) Int. Cl.
*A61B 5/0432*    (2006.01)
*A61B 5/04*    (2006.01)
(52) U.S. Cl.
CPC ..... *A61B 5/04011* (2013.01); *A61B 2560/0223* (2013.01); *A61B 2560/0228* (2013.01); *A61B 5/0432* (2013.01)
USPC ........................................................ 600/512

(58) Field of Classification Search
USPC .......................................................... 600/512
See application file for complete search history.

(56) References Cited

U.S. PATENT DOCUMENTS

| 4,587,976 A * | 5/1986 | Schmid et al. ................ 600/512 |
| 5,749,367 A | 5/1998 | Gamlyn et al. |
| 2004/0111021 A1 | 6/2004 | Olson |

FOREIGN PATENT DOCUMENTS

| EP | 1108390 | 6/2001 |
| WO | 99/36860 | 7/1999 |
| WO | 03/057031 | 7/2003 |
| WO | 2006/011144 | 2/2006 |

* cited by examiner

*Primary Examiner* — Carl H Layno
*Assistant Examiner* — Jon Eric C Morales
(74) *Attorney, Agent, or Firm* — Rankin, Hill & Clark LLP

(57) ABSTRACT

A method for calibrating a diagnostic measuring device for biological signals, which can be represented as vectors, such as the representation of cardiac potentials in cardiography. The method determines a zero-point vector or reference point for the calibration of the measuring device as an average vector within a resting section having minimal change of the signal. A search range for such a resting section can be limited to a time frame within the entire measuring period and biologically justified, for example, by means of empirical data that indicate physiological resting phases and/or from the knowledge of the course of the physiological process to be examined.

16 Claims, 2 Drawing Sheets

METHOD FOR CALIBRATING A DIAGNOSTIC MEASURING DEVICE

BACKGROUND OF THE INVENTION

1. Field of the Invention

The invention relates to a method for calibrating a diagnostic measuring device for biological signals, which can be represented as n-dimensional vectors. In medical diagnostics, such measuring devices are for example known in electroencephalography or in all fields of cardiography and vector cardiography and cardiogoniometry.

2. Description of Related Art

Such measuring devices and their diagnostic significance are, for example, based on measuring the electrical activity of an organ, with this activity differing in the healthy and sick state. In the case of the heart, cardiography is based on an electric field generated by membrane flows in the myocardial cells. The (sum) vector of this electric field generated by the heart varies over time in respect of its magnitude and its spatial orientation. The cardiac cycle, i.e. the electric progression of each heartbeat, can be subdivided into various segments. In a conventional electrocardiogram, the P-wave corresponds to the atrial excitation, the R-wave corresponds to the ventricular depolarization and the T-wave corresponds to the ventricular repolarization.

In cardiogoniometry, as described in EP 0 086 429, the cardiac flows are captured in four mutually orthogonal projections using four thoracic electrodes close to the heart in order to measure the magnitude of the potentials and to locate these in space. EP 1 048 000 presents a development of this teaching, which entails a computer-assisted computational analysis for improved representation and interpretation of the measurement results.

By way of example, the aforementioned P-, R-, and T-waves are represented as P-, R-, and T-vector loops in the spatial representation of vector cardiography or cardiogoniometry. These vector loops represent the path that the tip of the electric field vector generated by the heart passes over during the time of one heartbeat. The sum vector of the electric field generated by the heart over time runs over three loops in 3D space. The origin of the sum vector can be imagined to be a null point of a coordinate system for this space. This null point has to be defined because different measured values arise depending on the selection of the null point.

Firstly, the null point should correspond as closely as possible to a physiologically based null value and secondly it should be able to be established reliably despite the variability in the myocardial activity as a result of individual differences, a state of exertion, medical condition, etc. Moreover, various interfering influences such as e.g. offset voltages have to be filtered out. In such a physiological system, it is accordingly difficult to find a reliable null point as a reference point for calibrating the measuring device.

BRIEF SUMMARY OF THE INVENTION

It is therefore the object of the invention to provide a method for calibrating a diagnostic measuring device for representing biological signals, more particularly biological potentials, as n-dimensional vectors, which method overcomes this difficulty in finding a reliable definition of the null point which is also as reasonable as possible from a biological point of view. This object is achieved by a method as defined in the independent claim. The dependent claims define advantageous embodiments of the invention.

The method according to the invention for calibrating a diagnostic measuring device relates to measuring devices that generate a sequence of measured values that can be represented as n-dimensional vectors. Here, n assumes a value of at least 2. A search region is defined for a rest segment contained in this search region. The search region is defined as the region in which a rest segment is sought. The rest segment is a segment in which there is little change in the vector. This rest segment and a mean vector lying in this rest segment are established from measured values obtained in the search region. The mean vector in the rest segment is set as a reference vector for calibrating the measuring device.

In this patent document, the term "diagnostic measuring devices" comprises not only measuring devices for making a diagnosis but rather measuring devices from all fields of human and veterinary medicine, more particularly also measuring devices that are used in therapeutic and surgical applications.

A basic idea of the invention is to define the null point vector or reference point (reference vector) for calibrating the measuring device as a mean vector which preferably lies In the middle of a time segment—called a rest segment—during which there is minimal change in the magnitude of the vector. Such a rest segment may lie in a biologicaliy based rest phase like e.g. a rest phase in a repetitive biological cycle, as in the case of the above-described heartbeat. However, the rest segment may also correspond to a rest phase in the signal that can be determined by empirical means only, without causal relationships for this rest phase necessarily being known. In the case where the rest phase is determined empirically, a temporal search region is determined for the rest segment that contains an empirically determinable and/or physiologically based rest phase in the signal output. However, it is also possible to search for a rest segment in the whole time span of the measurement.

By way of example, the change in the measured values per unit time serves as measure for the change in the signal. In very general terms, a measure is obtained in respect of how far the measured values deviate from a mean value during a comparison time segment. By way of example, the arithmetic mean of the values of the deviations may be used as such a measure; however, it is also possible to use the variance or the standard deviation or other mathematically reasonable measures for the average deviation. In the following text, the term change in the measured values is used, as a generalization, for each reasonable measure for the average deviation from a mean value.

When the rest phase is determined empirically, the change in the measured values during a time segment delta can be compared to the change in the measured values during other time segments and the time segment with minimal change in the measured values can be identified as the rest segment. The time segments delta can be selected over the course of the measurement as "moving windows" or as overlapping or singular time segments delta around selected measurement times. Depending on the application, different conditions can be demanded in respect of the change in the measured values within a time segment delta in order to satisfy the criterion for a "rest segment". By way of example, such criteria include that the mean deviation (arithmetic mean of the values of the deviations, standard deviation, variance, etc.) from the mean value In the comparison time segment of the measured values in the rest segment is at most a third of, preferably at most half of and particularly preferably at least one order of magnitude smaller than the mean deviation in comparison time segments outside of the rest phase.

It is self-evident that a person skilled in the art will expediently define the comparison time segments or moving windows such that they approximately correspond to the size of the expected rest phase in order to prevent averaging over rest and active phases. The duration of the comparison time segments is typically selected such that said segments contain a multiple of the periods of characteristic signal fluctuations, but at most are a small fraction (e.g. at most 1/10 or at most 1/20) of a whole cycle. In the case of cardiac signals, the comparison time segments will, for example, preferably have a duration of between 5 ms and 100 ms, preferably between 10 ms and 50 ms, particularly preferably between 15 ms and 30 ms, e.g. 20 ms. In the general case (i.e. not only relating to cardiac signals), the periods of characteristic signal fluctuations can, for example, be determined by Fourier transform (the sought-after period corresponds to the inverse of the frequency at which the Fourier spectrum has a maximum), with the visual estimation by a person skilled In the art often allowing for a better comparison time segment duration to be set than if a mathematical algorithm is used.

The search region can contain the whole measurement period, i.e. for example measured values over at least one whole signal cycle, or else it can comprise only part of the measurement period. It is also possible initially to carry out this method for finding a rest segment over relatively large time segments and then to repeat it within a then-identified rest segment, which leads to an increasing refinement of the method for identifying the rest point.

Thus, according to a preferred embodiment, it is possible to identify a rest segment within any search region in which a rest phase is present. This holds true both if the search region contains the whole measurement period and also if it only comprises part of the measurement period.

According to a further preferred embodiment, the search region for a rest segment will not comprise the whole course of the measurement, but will be restricted to a biologically reasonable time span within the whole course of the measurement. By way of example, a biologically based search region may be established from empirical data which indicate physiological rest phases and/or from the knowledge of the sequence of the physiological process to be examined, more particularly in respect of the phases thereof with no or only minimal physiological activity. Such a restriction of the search region directs the rest segment with a minimal change in the measured values of the signal and the mean vector in the center of this rest segment to a physiological rest phase.

A great advantage of this method for calibrating a measuring device is that it can be applied to all recordings of biological signals that can be represented by n-dimensional vectors, for example by two-dimensional or three-dimensional vectors or as multichannel n-tuples, which represent a measured value at a specific time. The known 12-channel EKG is mentioned here as an example of a multichannel application. In vector cardiography, the sum vector of the electric field generated by the myocardium is represented by a three-dimensional vector.

The following text describes the method for calibrating a measuring device in detail using the example of cardiography and more particularly vector cardiography, with this not meaning that the invention is restricted to cardiographic applications.

A physiologically based null point, which is therefore suitable as a reference point for calibrating a measuring device for the electric cardiac activity, is situated at the point with the smallest possible electric potential after all excitations have died down and no new ones have started yet. The null point, satisfying this condition, as a reference point for the calibration is correspondingly defined as an isoelectric null point. If this null point were to correspond to the isoelectric null point, the measurement of the vector of the electric field generated by the heart during a rest phase would theoretically result in a potential of 0 volt in all leads. However, as mentioned at the outset, the measured potentials from the leads are falsified by interference in the measurement system, and so a measurement of precisely 0 volt in all leads is never measured, even at an exact measurement time at which a completely isoelectric potential is present. The method according to the invention can be used to establish the null point as a reference point for the calibration such that it corresponds to the isoelectric null point to the best possible extent, i.e. that a potential of 0 V is, as a best approximation, always indicated in the measurement data when there actually was a rest potential at the body.

During the cardiac cycle, the vector of the electric field generated by the heart respectively approaches the theoretically defined isoelectric null point during a number of short rest phases, particularly in the phases after the atrial excitation (P-wave) and before the ventricular depolarization (R-wave), i.e. just before the so-called Z-point, and also after the depolarization and before the repolarization of the ventricle (T-wave) at the so-called J-point, and, once again, after the ventricular repolarization and before the atrial excitation of the next beat. The rest phase before the depolarization of the ventricles (R-wave) is of the greatest importance for determining the isoelectric null point because the conduction of the electrical activity in the AV node rests at this time and hence the Z-point has not yet been achieved and action potentials from ventricular myocardial cells are not yet discharging and -there has not yet been the onset of the repolarization of the atrial cells either.

Furthermore, the invention is based on an observation that was made from recordings, found in studies, of the rest state of approximately 1000 patients, namely that there is a significant period of time between the atrial excitation (P-wave, P-loop) and ventricular depolarization (R-wave, R-loop) in almost all recordings of potential profiles from the patients, during which time the measured vector of the electric field generated by the heart undergoes little change. That is to say, a number of successive measurement points from all leads supply constant values, which, during this time span, are distributed around an imagined center point. This time span with an isoelectric potential therefore corresponds to a rest phase with minimal change in the vector and, depending on the person, usually has a duration of between 20 ms and 80 ms, or even longer.

Since, as explained above, the physiology of the heart also predetermines such a rest phase prior depolarization, the search region is selected preferred embodiments of the method such that it includes this rest phase, but is not extended to whole time profile of a heartbeat. By way of example, it extends from the potential maximum of the atrial excitation to the maximum of the ventricular depolarization. The search region can also be selected to be smaller, provided it is ensured that it includes the rest phase. The rest segment and the mean vector as a null point vector or reference vector situated in the center thereof are now established within the defined search region on the basis of the raw data by using a numerical method. This procedure ensures that the null point, as reference point for calibration, falls into the physiological rest phase before the ventricular depolarization (R-wave, R-loop) and, to the best possible approximation, corresponds to the isoelectric null point.

A further advantage for cardiologic applications of this method is that even if the rest phase before the ventricular depolarization is only very short this occurs in some patients—it is nevertheless possible to establish a physiologically reasonable null point as a reference point for calibration. By applying a numerical method as described below in an exemplary fashion, a null point is established at which the time profile of the vector changes the least quickly, i.e. is most at rest. Hence the method is not very susceptible to errors. The only minimum requirement is that the R-wave of the beat has already been uniquely localized, wherein an approximate and not yet precise localization may already suffice.

A further advantage of the method is that the applied calculation of a null point as reference point is also invariant with respect to a rotation and translation of the measured values. It can be applied both directly to unprocessed samples of a measurement and also to filtered or smoothed or averaged measurements, and supplies the same good results in all cases.

The method according to the invention is also suitable for calibrating measuring devices from outside the field of cardiology, for example from electroencephalography for measuring the electrical activity of the brain, wherein, analogously to the discussion above, the search region for the reference null point should accordingly be selected such that a physiological rest segment can be expected therein. Further applications of the method according to the invention relate to the calibration of measuring devices for other biological processes such as hormonal or other chemical or physical processes during which measurement data is collected over a time segment and related to a reference point.

A further aspect of the invention relates to a measuring device which measures biological signals such as e.g. potentials and comprises means for carrying out the method as described above. A preferred embodiment of a measuring device measures potential changes in a human or animal organ such as the heart or the brain by means of electrodes, e.g. on the body surface, by deriving the signals and capturing, processing and recording these signals as measured values using instruments or instrument components known from the prior art. These instruments or instrument components have means for applying the method according to the invention for calibrating the measuring device. This means that the measured values are corrected by the magnitude of the reference vector established in the method according to the invention before the measured values are finally displayed. The means for applying the method according to the invention could, for example be the programming of the instrument or an instrument component, or a software component.

BRIEF DESCRIPTION OF THE DRAWINGS

Exemplary embodiments of the method will be described in more detail in conjunction with the following figures.

DETAILED DESCRIPTION OF THE INVENTION

Figure 1:
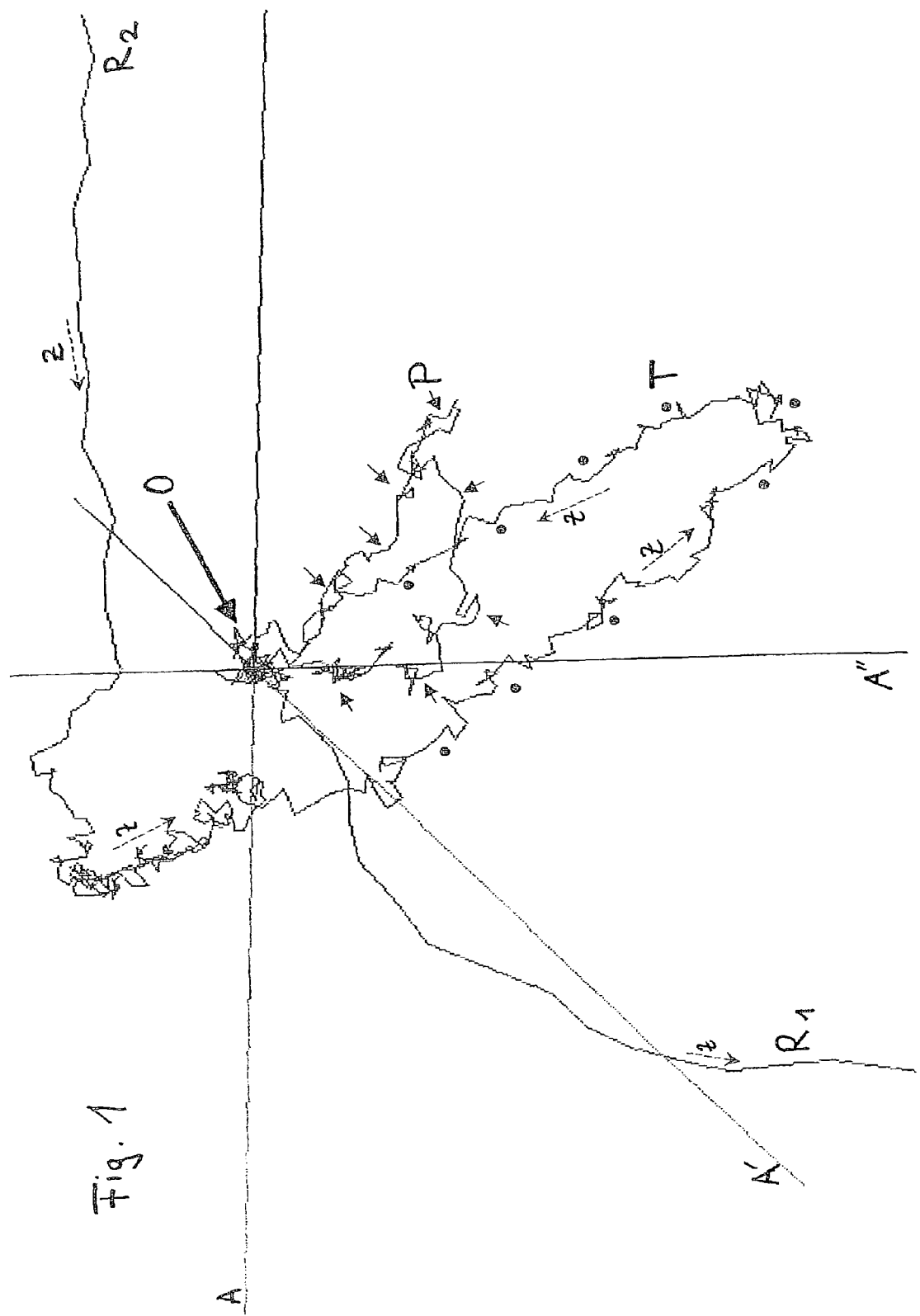
FIG. 1: A magnified section of a spatial recording of a heartbeat, which indicates vector loops and resting vector clusters from a vector cardiogram.

FIG. 1 relates to the application of the method to a measuring device for vector cardiography. It shows a magnified section of a spatial representation of the heart potentials, in which the vector of the electric field generated by the heart was established for every time t. The vector cardiogram shows the connecting line between the tips of these vectors from one measured sample to the next. Here, each cardiac cycle produces a number of characteristic loops that are interrupted by phases during which the vector (i.e. the magnitude and spatial orientation of the electric field) remains relatively constant. Such a rest phase is visible in FIG. 1 like a cluster of short lines (i.e. connecting lines from vector to vector), which wander virtually without direction around a center point 0 (marked by a long arrow) or only scatter in the microvolt region. Before the rest phase, prior to the R-loop considered here, the vector wanders into this "resting cluster" coming from the P-loop P (marked by eight short arrows), and after this rest phase it emerges from the cluster and leaves the null point very quickly and to a great distance in order to pass through the R-loop at great speed ($R_1$ marks the limb of the R-loop leading away from the null point). The end of the R-loop ($R_2$) and the subsequent T-loop T (marked by dots) are likewise illustrated in the figure. The isoelectric null point 0 lies in the geometric center of the cluster prior to the R-loop, and the coordinate origin has been placed onto the isoelectric null point. The three orthogonal axes A, A' and A", which define the 3D space in this case, intersect at the null point as per the definition. The dashed, lance-shaped arrows Z along the loops specify the temporal course of the propagation of the field vector in space.

The method according to the invention for calibrating a diagnostic measuring device for biological potentials can be applied to all methods for recording cardiac potentials, for example also to electrocardiography, and is not restricted to the embodiment for a spatial recording described in this figure.

Figure 2:
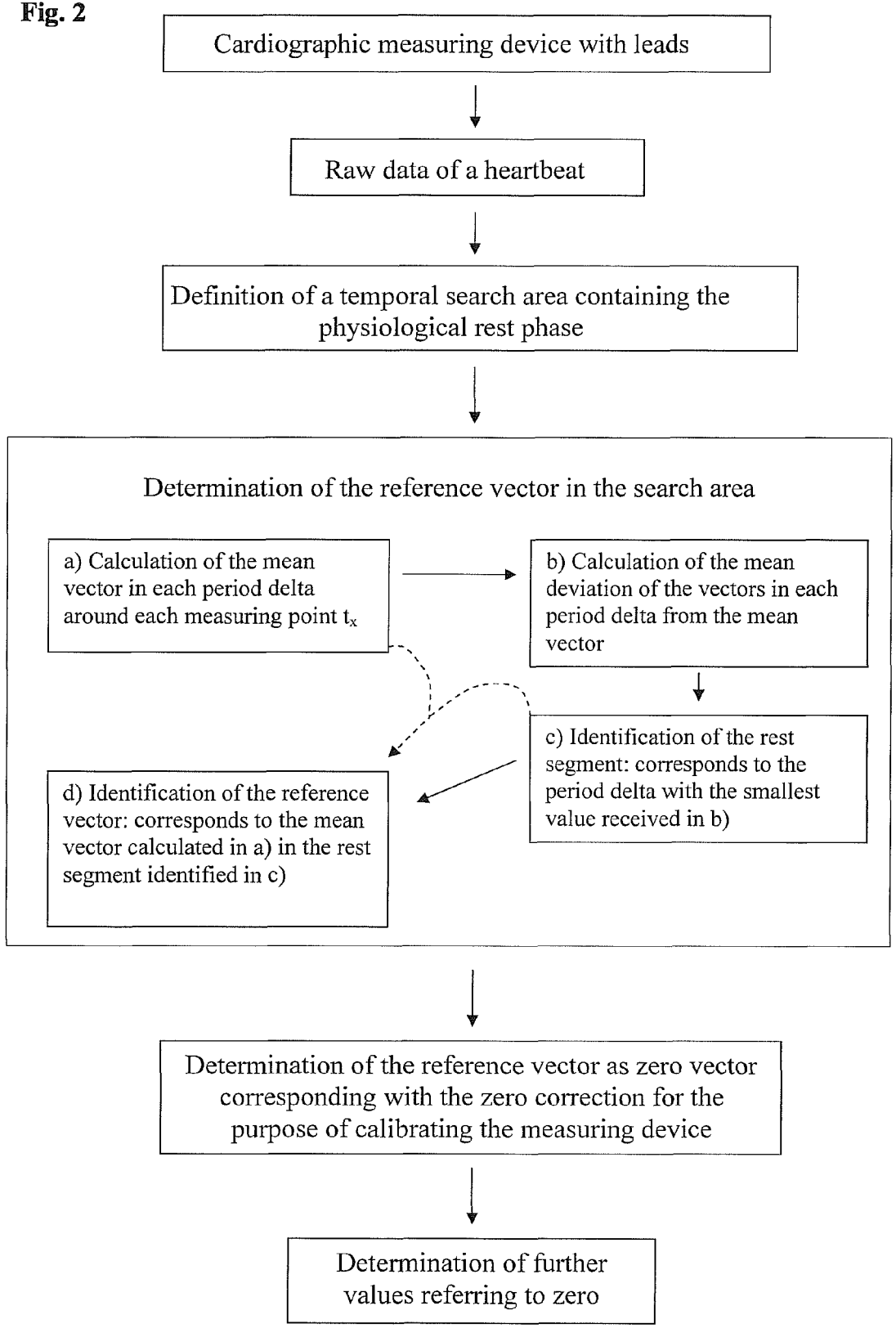
FIG. 2: A flowchart of an exemplary method for establishing a null point as reference point for calibration in accordance with the isoelectric null point as geometric center point of a resting vector cluster.

FIG. 2 shows a flowchart of an exemplary method for calibrating a vector-cardiographic measuring device, wherein the null point as reference point for calibration is identified as a geometric center point of a resting vector cluster.

In order to calibrate a cardiographic measuring device, a temporal search region is initially defined from the raw data of a cardiac cycle, within which search region a rest segment should be found. The search region needs to be large enough to contain a physiological rest phase and at most extends from the potential maximum of the atrial excitation (tip of the P-loop) to the potential maximum of the ventricular depolarization (tip of the R-loop). However, the search region can also be selected to be smaller, provided it is ensured that it contains a rest segment.

A number of times $t_x$ for $x=1 \ldots n$ are subsequently selected within this search region. The null point vector is established numerically from the measured values of the signal vectors during time intervals delta around these times $t_x$ and it is used as a reference vector for the calibration.

A possible variant for establishing this by numerical methods for example comprises steps a)-d):

a) define a temporal neighborhood delta around every one of the selected times $t_x$ for $x=1 \ldots n$ with a number of measurement times within the time interval delta (starting at the time $t_x$–delta/2 up to the time $t_x$+delta/2, etc.) and determine the magnitude of the vector that expresses the electric field generated by the cardiac muscle for each of these measurement times. Calculate the magnitude of the mean vector in the time interval $t_x$–delta/2 to $t_x$+delta/2 by adding all vector magnitudes and subsequently dividing by the number of vectors. The result is the magnitude of the mean vector in the time interval delta around the time $t_x$. This mean vector magnitude is established for each time interval delta around everyone of the times $t_x$ for $x=1 \ldots n$ in the search region.

b) Calculate the mean deviation of all vector magnitudes in the time interval from $t_x$–delta/2 to $t_x$+delta/2 from the mean vector calculated in a) by subtracting the latter from each individual vector of the vectors established at all measurement times and by determining the respective magnitude of the arising difference vectors. These magnitudes are once again summed and divided by the number of summed magnitudes. The result is the mean deviation of these vectors from the mean vector calculated in a. This mean deviation is a measure for the mean speed at which the sample vectors move in the time interval $t_x$–delta/2 to $t_x$+delta/2. This mean deviation or speed is calculated for each time interval delta around each time $t_x$ in the search region.

c) Compare the mean speed of the vectors (calculated in b)) at each measurement point over the whole search region and identify the time interval delta with the smallest mean speed of the vectors. This time interval delta is the sought-after rest segment with the measurement point $t_x$ in the center thereof.

d) Identify the mean vector of the time interval t–delta/2 to t+delta/2 around this measurement point (calculated in a) for this measurement point in the temporal center of the rest segment. This vector is the null point vector, which represents the rest potential of the measurement and is used as a reference vector for calibrating the measuring device.

The invention is not restricted to methods that apply a numerical calculation. according to this example. Depending on the application, it is possible, for example, to consider the following variants, either individually or—where possible—in combination:

dispensing with the selection of a search region; instead averaging over the whole region determining the variance or standard deviation in each of the time intervals instead of forming the arithmetic mean of the difference values applying weighted averaging, for example by taking greater or lesser account of points situated further away from the time $t_x$ selecting a different characteristic vector in step d), e.g. by selecting a specific measured value instead of a mean value (under the assumption that an individual measured value is already representative in the determined low change in the measured values during the rest segment)

selecting a time segment not identical to the time interval $t_x$ as rest segment. By way of example, it is possible to select a time segment that only contains a central region of the time interval and to calculate the average value therein, particularly if the time intervals are selected to be comparatively large. On the other hand, it is also possible to select a larger region that completely contains the time interval, for example if the rest segment is expected to lie in a relatively long time segment of relative rest.

The magnitude of the null point vector established in this method as mean vector of a resting vector cluster in practice corresponds to the difference between the measured potential during the rest phase and the isoelectric null point, and it can therefore be used in the calibration method as biologically reasonably justified null point correction.

The calibration or null point correction can be undertaken in various ways, as a person skilled in the art is aware of per se. In one embodiment of the method according to the invention, the null point vector or reference vector is subtracted from the vector of all measured values of a cardiac cycle or the whole measurement period. The null point vectors of a plurality of heartbeats are initially calculated in other embodiments; they are then averaged and the averaged null point vector is subtracted from the vector of each measured value. It is self-evident that the null point correction can also be carried out and represented graphically. By way of example, successive null point vectors can be connected by a straight line or by another expedient connection curve such as a spline or a numerically established approximation curve.

A further advantageous use of the null point determination is the calculation of the Z-point. In cardiology, the Z-point (zero point) describes the time at which the ventricular depolarization starts. Accordingly, it defines the start of the R-wave or R-loop. It should not be equated to the isoelectric null point, but is found just after the latter; hence the potential of the Z-point should not be corrected to 0 volt potential either. In terms of time, the Z-point should be located where the vector finally, in a spatial sense, leaves the cluster that represents the rest phase in order to pass through the R-loop. Accordingly, it is usually situated in the vicinity of the isoelectric null point and can be situated within or outside of the rest segment.

After the best possible null point corresponding to the isoelectric null point was found, the Z-point can also be found easily in a similar fashion: a temporal search region is defined, within which the Z-point should be found. The search region must be large enough to contain the Z-point and extends from the time of the lowest mean speed of the vector up to the point at which the magnitude of the vector has distanced itself by the value epsilon from the isoelectric null point and does not again come closer to the latter before the R-maximum. The value epsilon can be defined in microvolt and should have a suitable low value.

It is self-evident that any other points during the course of the cardiac cycle can also be established like this, provided it is possible to represent a dependence of such a point to the null point. It is self-evident that such a use of the method according to the invention can also be transferred to the measurement of other biological processes.

The invention claimed is:

1. A method for calibrating a diagnostic measuring device, comprising the steps of:
    generating a sequence of measured values with the measuring device that can be represented as n-dimensional vectors, with n having a value of at least 2,
    defining a search region, said search region having a rest segment contained therein, said rest segment being part of a rest phase,
    establishing the rest segment and a mean vector lying in said rest segment from measured values obtained in the search region, and
    setting said mean vector as a reference vector for calibrating the measuring device.

2. The method as claimed in claim 1, wherein the search region corresponds to a mean value of a plurality of periodically recurring measured value sequences.

3. The method as claimed in claim 1, wherein a time segment with a minimal change in the measured values is established in the search region and the rest segment is set such that it at least partly contains the time segment with a minimal change in the measured values.

4. The method as claimed in claim 1, wherein a restricted phase within a whole measurement period is defined as the temporal search region for the rest segment.

5. The method as claimed in claim 1, wherein a region is selected as the search region, the former region containing a physiologically based region with low physiological or biological activity.

6. The method as claimed in claim 1, wherein the measuring device is suitable for recording electrical activity of a cardiac muscle.

7. The method as claimed in claim 6, wherein a temporal search region for the physiologically based rest segment extends from a potential maximum of an atrial excitation to a potential maximum of a ventricular depolarization of a cardiac cycle.

8. The method as claimed in claim 1, wherein a whole measurement period or at least a whole signal cycle is selected as the search region.

9. The method as claimed in claim 1, wherein a reference vector for calibrating is established using a numerical method, which carries out at least the following four steps in the search region with a number of selected times:
   a) calculating the mean vector in a time segment delta around each selected time in the search region;
   b) calculating a mean deviation of all vectors from the mean vector in the time segment delta;
   c) identifying the rest segment as time segment delta with the smallest mean deviation of all vectors from the mean vector;
   d) identifying the reference vector as the mean vector in the time segment delta identified as rest segment.

10. The method as claimed in claim 9, wherein at least one characteristic measurement point is determined from the sequence of measured values generated by the diagnostic measuring device, with the established reference vector serving as a reference point for determining said characteristic measurement point.

11. The method as claimed in claim 10, wherein the characteristic measurement point is a Z-point, wherein the Z-point is defined as the first measured value, lying after the null point, whose magnitude at least corresponds to a threshold epsilon in the coordinate system with the reference vector as null point and which no longer undershoots said threshold epsilon.

12. A device for measuring biological signals, wherein at least one component of the measuring device has means for carrying out the method as claimed in claim 1.

13. The device as claimed in claim 12 for measuring biological signals, wherein the signals are potentials and the device comprises at least two electrodes and an instrument or instrument components for capturing measured values corresponding to signals of these electrodes and also for processing measured values and for representing the processed measured values.

14. The device as claimed in claim 13, wherein it is a cardiographic or cardiogoniometric device.

15. A measuring device that is configured to measure biological signals, said device being adapted to:
   generate a sequence of measured values with the measuring device that can be represented as n-dimensional vectors, with n having a value of at least 2,
   define a search region, said search region having a rest segment contained therein, said rest segment being part of a rest phase,
   establish the rest segment and a mean vector lying in said rest segment from measured values obtained in the search region, and
   set said mean vector as a reference vector for calibrating the measuring device;
   wherein the measuring device is suitable for recording electrical activity of a cardiac muscle; and,
   wherein a temporal search region for the physiologically based rest segment comprises the period from a potential maximum of an atrial excitation to a potential maximum of a ventricular depolarization of a cardiac cycle.

16. The measuring device as claimed in claim 15, wherein the signals are potentials and the device comprises at least two electrodes and an instrument or instrument components for capturing measured values corresponding to signals of these electrodes and also for processing measured values and for representing the processed measured values.

* * * * *